US009603535B2

United States Patent
Orron et al.

(10) Patent No.: US 9,603,535 B2
(45) Date of Patent: Mar. 28, 2017

(54) METHOD AND SYSTEM FOR DETERMINING LIFE THREATENING CONDITION VIA BODILY WORN SENSORS

(71) Applicant: Life BEAM Technologies Ltd., Tel-Aviv (IL)

(72) Inventors: Zvi Orron, Tel-Aviv (IL); Yoav Aminov, Tel-Aviv (IL); Omri Yoffe, Sde Warburg (IL); Elad Hofstetter, Tel-Aviv (IL)

(73) Assignee: LifeBEAM Technologies Ltd., Tel-Aviv (IL)

( * ) Notice: Subject to any disclaimer, the term of this patent is extended or adjusted under 35 U.S.C. 154(b) by 67 days.

(21) Appl. No.: 14/601,279

(22) Filed: Jan. 21, 2015

(65) Prior Publication Data
US 2015/0201850 A1 Jul. 23, 2015

(30) Foreign Application Priority Data

Jan. 21, 2014 (IL) .......................................... 230578

(51) Int. Cl.
| | |
|---|---|
| A61B 5/02 | (2006.01) |
| A61B 5/0205 | (2006.01) |
| A61B 5/026 | (2006.01) |
| A61B 5/0488 | (2006.01) |
| A61B 5/11 | (2006.01) |
| A61B 5/00 | (2006.01) |
| A61B 5/021 | (2006.01) |
| A61B 5/024 | (2006.01) |
| A61B 5/053 | (2006.01) |
| A61B 5/08 | (2006.01) |

(52) U.S. Cl.
CPC ........ *A61B 5/02055* (2013.01); *A61B 5/0261* (2013.01); *A61B 5/0024* (2013.01); *A61B 5/021* (2013.01); *A61B 5/02416* (2013.01); *A61B 5/0488* (2013.01); *A61B 5/0531* (2013.01); *A61B 5/0816* (2013.01); *A61B 5/1118* (2013.01); *A61B 5/7282* (2013.01); *A61B 5/746* (2013.01); *A61B 2560/0242* (2013.01); *A61B 2562/0219* (2013.01)

(58) Field of Classification Search
CPC ........................... A61B 5/0205; A61B 5/0261
See application file for complete search history.

(56) References Cited

U.S. PATENT DOCUMENTS

| | | | | |
|---|---|---|---|---|
| 6,558,050 | B1 * | 5/2003 | Ishibashi | ............... G08B 15/004 348/158 |
| 7,286,753 | B2 * | 10/2007 | Yamasaki | ............ G02B 27/017 348/61 |

(Continued)

*Primary Examiner* — Eric D. Bertram

(57) ABSTRACT

A system for determining a life threatening condition of a human may include at least one mobility sensor couplable to a human body and configured to measure mobility parameters of said human body; at least one physiological sensor couplable to a human body and configured to measure physiological parameters of said human body; at least one environmental sensor configured to measure environmental parameters indicative of an environment of said human body; and a computer processor configured to apply a decision function configured to determine a predefined life endangering condition of said human body, based on said measured mobility, physiological, and environmental parameters, and statistical relationship therebetween.

13 Claims, 4 Drawing Sheets

(56) References Cited

U.S. PATENT DOCUMENTS

| | | | | |
|---|---|---|---|---|
| 2003/0025798 A1* | 2/2003 | Grosvenor | ............. | G06F 3/012 |
| | | | | 348/207.99 |
| 2008/0081958 A1* | 4/2008 | Denison | ............... | A61N 1/3706 |
| | | | | 600/300 |
| 2008/0188763 A1* | 8/2008 | John | .................... | A61B 5/0452 |
| | | | | 600/516 |

\* cited by examiner

METHOD AND SYSTEM FOR DETERMINING LIFE THREATENING CONDITION VIA BODILY WORN SENSORS

CROSS REFERENCE TO RELATED APPLICATIONS

This application claims the benefit of Israel Application Serial No. 230578, filed on Jan. 21, 2014 and entitled "METHOD AND SYSTEM FOR DETERMINING LIFE THREATENING CONDITION VIA BODILY WORN SENSORS", which is incorporated in its entirety herein by reference.

FIELD OF THE INVENTION

The present invention relates generally to the field of bodily worn sensors and in particular to such sensors that are used to deduce a life threatening condition.

BACKGROUND OF THE INVENTION

Security personnel and other first responders occasionally operate in a high risk zone or disaster area or may even be under a high risk of attack and ambush. In these scenarios, the security personnel could be subjected to severe body injury and even death caused by any sorts of events such as: floor collapse, accident, fire trap, explosives and the like. These events may prevent the personnel from reacting, rescuing themselves and even calling for help. In addition, a large scale event will create confusion in the front command room, blur the real picture of the ongoing events and delay backup or rescue team arrival.

Many sensors are known to be able to monitor various types of vital signs that may be indicative of the health condition of humans. However, a full deduction of acute conditions is very difficult to derive currently known vital signs sensors when attached at a single location to the human body.

SUMMARY OF THE INVENTION

According to some embodiments, a system for determining a life threatening condition of a human is provided herein. The system may include at least one mobility sensor couplable to a human body and configured to measure mobility parameters of said human body; at least one physiological sensor couplable to a human body and configured to measure physiological parameters of said human body; at least one environmental sensor configured to measure environmental parameters indicative of an environment of said human body; and a computer processor configured to apply a decision function configured to determine a predefined life endangering condition of said human body, based on said measured mobility, physiological, and environmental parameters, and statistical relationship therebetween.

Additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

Figure 1A:
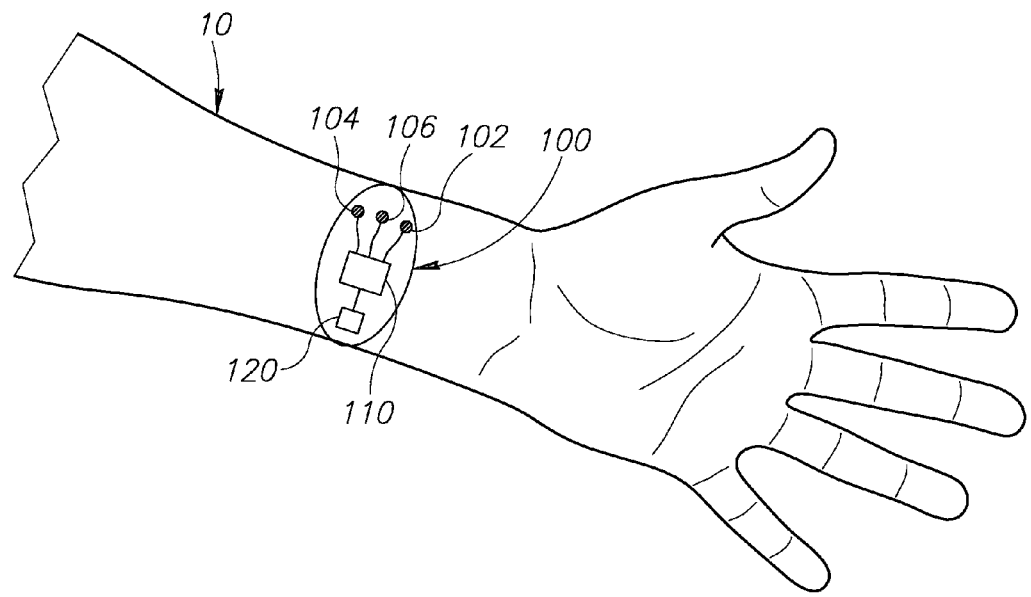
FIG. 1A is a schematic illustration of a system according to some embodiments of the present invention.

The drawings together with the following detailed description make the embodiments of the invention apparent to those skilled in the art.

DETAILED DESCRIPTION OF THE INVENTION

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before the embodiments of the invention are explained in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

Described herein are a method and system for detecting severe injury or death using environmental, physical, and physiological sensors. In one embodiment, the system may be embedded in a wrist watch. Alternatively, the system may be attached to many other body locations of the sensing system. In some configurations, the system may be implemented in a two part format, for example, one on the wrist, and one on the belt.

In order to achieve the ability to deduce an occurrence of an attack or ambush, the alert system is based on a platform of sensors that may include: mobility sensors, ambient sensors, and physiological sensors. All sensors measures are fused onto a decision function that derives, inter alia, statistical relationships between the different types of sensed metrics.

FIG. 1A is a schematic illustration of a system 100 according to some embodiments of the present invention. The system may be attached to an arm 10 of a human user 10 possibly near the wrist, and include a plurality of sensors of various kinds 102, 104, 106 as will be detailed below. The sensors are connected to a computer processor 110 on which a decision function is being executed. Additionally, a transceiver 120 is further connected to computer processor 110 for communicating with a control center or similar devices such as 100 attached to other human users.

Figure 1B:
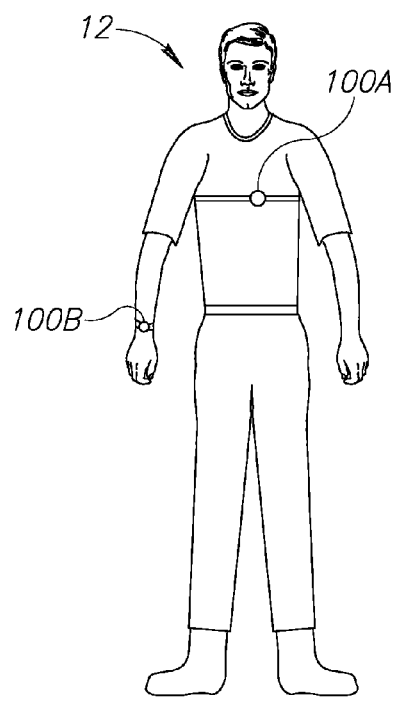
FIG. 1B is a schematic illustration of a system according to some embodiments of the present invention.

FIG. 1B is a schematic illustration of an aspect according to some embodiments of the present invention. The system may be attached in one device 100A to the torso (or other location) of user 12 while another device 100B may be connected to the wrist. The measurements are then averaged or subtracted to yield a more accurate measurement.

Figure 2:
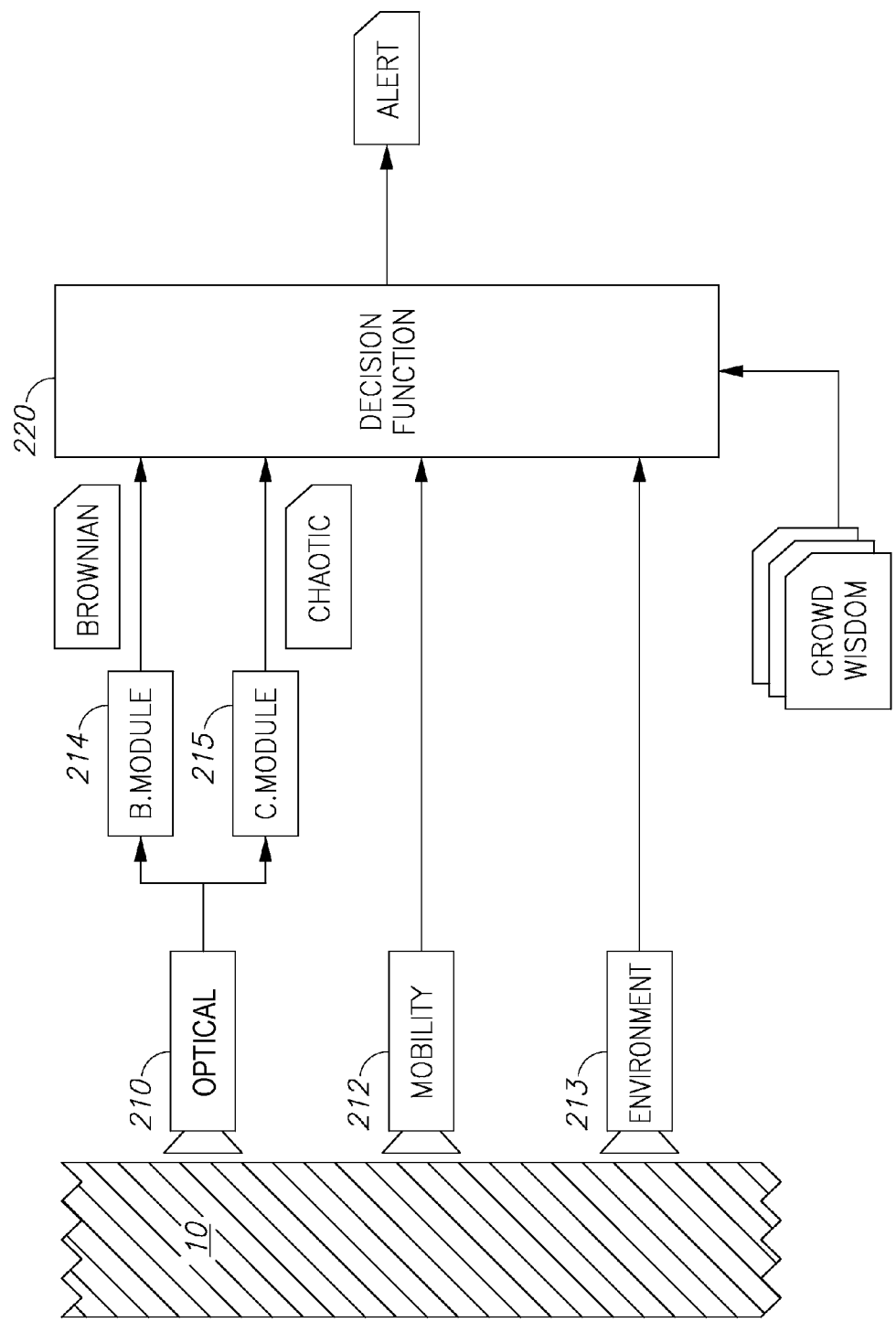
FIG. 2 is a block diagram of a system according to some embodiments of the present invention.

FIG. 2 is a block diagram of a system according to some embodiments of the present invention. The system may include at least one mobility sensor 212 couplable to a human body 10 and configured to measure mobility parameters of said human body 10. The system may further include at least one physiological sensor such as a sensor that is based on any kind of an optical sensor 210 couplable to human body 10 and configured to generate a so-called optical signal based on which, physiological parameters of said human body are measured. In one embodiment, the optical signal is applied to a Brownian motion module 214 which is configured to indicate a level of variation between the optical signal, representing the blood flow, and a Brownian motion. In one embodiment, the optical signal is also applied to a chaotic movement module 215 which determines how a level of chaotic movement of the blood.

The system may further include at least one environmental sensor 213 configured to measure environmental parameters indicative of an environment of said human body. The system may further include a decision function 220 implemented by a computer processor configured to determine a predefined life endangering condition of the human body 10, based on said measured mobility, physiological, and environmental parameters, and statistical relationship therebetween which are also being computed by the computer processor. An alert may be issued once the life endangering conditions are beyond a predefined threshold. Data from other users of a similar device may be derived as crowd wisdom, to assist decision function 220.

According to some embodiments of the present invention, the mobility sensors may be configured to detect major changes in activation of the user, such as fall down, no movement, change of posture, detect a nearby blast or gun shot and detect unplanned change in GPS location.

According to some embodiments of the present invention, the physiological sensors may be configured to detect changes in vital signs metrics such as: blood flow, electromyography (EMG) body and skin temperature, skin conductance, heart rate, respiration rate, and blood pressure.

According to some embodiments, a decision function may be configured to receive the outputs of the platform sensors and detect the deviation from a specified patent of normal condition such that whenever the deviation is above a predetermined threshold, an alert signal may be issues and possibly transmitted to front command room to call for rescue. The use of the aforementioned sensing platform is specifically relevant for first responders and other occupations such as firefighters, policemen, miners, and security personnel such as soldiers and any other military personnel.

According to some embodiments of the present invention, the mobility detectors may be implemented by accelerometers to determine possible death or severe injury and may be positioned over several locations on the body. Even while asleep, the human body is in motion—breath, pulse and muscle tone. At death or syncope, skeletal muscles are relaxed, and the tonus is reduced. In some embodiments, the sensing platform may use highly sensitive accelerometers on several locations on the body to detect the slightest motion and distinguish between faint physiological body motions, and no motion at all caused by death or tone-less syncope.

According to some embodiments, the accelerometers and gyro are used together in order to detect different activation states. Accelerometers and gyro sensors are used to determine the subject's activity such as walking, running, standing, laying down, crawling and the like. The sensors may be attached in a plurality of different locations on the body, enabling high sensitivity in the activity identification.

According to some embodiments, the physiological sensors may include of Electromyography (EMG) sensors configured to determine possible death or severe injury (all over the body). In EMG, the electrical activity produced by skeletal muscles is evaluated and recorded. The signals can be analyzed to detect medical abnormalities, activation level, and recruitment order or to analyze the biomechanics of human or animal movement. At death or syncope, skeletal muscles are relaxed, and the tonus is reduced. Experiments carried out by the inventors have shown significant results in distinguishing between a person's static state and death. According to some embodiments, the sensing platform may use EMG signal acquired from any muscle to detect possible death or pass out of the subject.

In some embodiments, the optical sensor is configured to sense only the moving red blood cells (RBC). It senses the derivative of RBC velocities and thus can monitor very slow and shallow blood flow that is typical to situations such as severe injury or death.

Some embodiments of the present invention may use optical sensors to detect massive blood loss due to severe injury and detect possible death based on two parameters derived from the optical sensor. The first parameter is how much is the blood flow distant in its behavior from a Brownian motion. The second parameter is the likelihood of pulsation artifacts in the optical signal.

A straightforward approach to validate vitality of a human being is to measure the pulse amplitude, for example, using standard PPG sensor. However, while in most of problematic situation, where an exact assessment is most needed, the pulse amplitude is very weak (injury or death).

Moreover, when the signal is measured on the wrist, the pulsatile component is frequently not very prominent from the very beginning, so the measurement of the pulse can't be used as a robust solution to the blood flow estimation problem. Moreover, zero pulse amplitude doesn't mean that the blood flow is stopped. It means that the pulsatile component of the signal cannot be observed. Therefore, the blood flow estimation problem is simplified to the evaluation of the very existence of the substantial blood flow signs. As long as the heart pump pushes the blood, the red blood cells continue to circulate through the vessels.

In accordance with some embodiments of the present invention, a new approach addressing the aforementioned blood flow estimation problem is presented, based on two main parameters as follows:

The first parameter is an evaluation of proximity of the measured blood flow to a Brownian motion. It is assumed that the very extreme case, where the blood flow is zero, the Brownian motion becomes dominant. Brownian motion can be evaluated by the measuring of a decay time of the autocorrelation function of the optical signal. The longer this decay time, the closer is the blood movement stage to the Brownian conditions.

The second parameter is a chaotic flow analysis. Under normal laminar blood flow conditions, the blood moves concurrently at different arterioles. At another extreme case where the heart fails to push the blood, a chaotic vessels constriction (biological zero) prevails, which makes the movement of red blood cells particles at different arterioles to be mutually uncorrelated. The more chaotic the movement, the higher is the probability of low vitality stage.

In one embodiment, a combined vitality index (CVI) can be used. The CVI takes into consideration these two parameters and evaluates a measure of Vitality. Experimental results show that CVI index can be used as a good indication of a lack of flow for all sites and cases even if the initial flow if very low.

In accordance with some embodiments, group monitoring may also be used in order to improve the data collection and analysis. Since the personnel operate frequently in groups (pairs and squads), a change in a subjects physiological state without a similar changes in other persons in the group can indicate an event. Additionally, an event occurred to one of the group might indicate the state of the others.

According to some embodiments, wisdom of the crowd algorithms can firstly be used to compare between the statuses of each subject in the group with his or her companions. Then, bits of information which may include both physiological and environmental conditions from several members of group are combined to form a larger picture of the group's status. In particular, an abnormal behavior of a group may be compared with a normal behavior of a similar group performing a collaborative task with similar characteristics.

According to some embodiments, the aforementioned sensors are designed as low power sensors. Physiological and optical sensors are usually more energy consuming. Some embodiments of the present invention utilize highly sensitive but less specific physical sensors which are very low powered to activate the physiological sensors. In this manner, when an event has occurred such as injury of the wearer, the physical sensors will detect the change and activate the physiological sensors which are more specific. In case this is a false alarm, the physiological sensors will detect so and return to hibernation after a short time. In this way, we can extend dramatically the battery life of the system.

Figure 3:
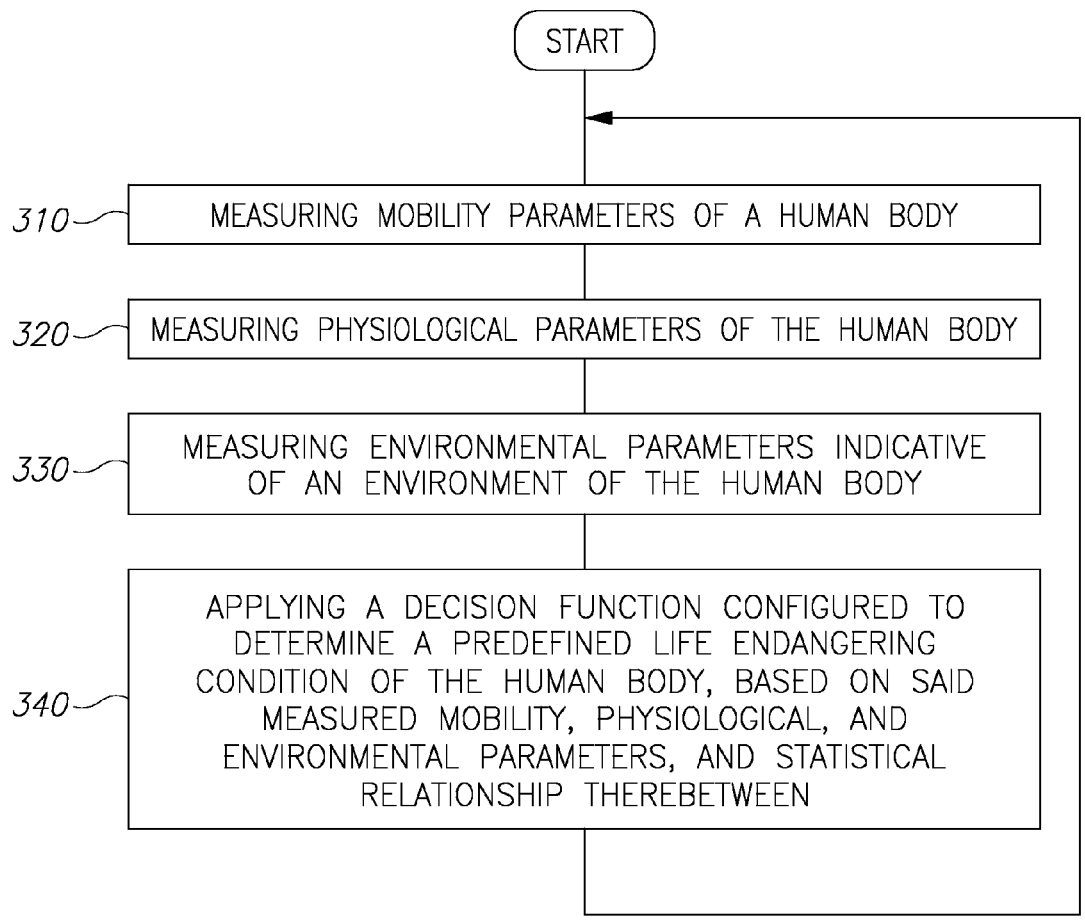
FIG. 3 is a high level flowchart of a method according to some embodiments of the present invention.

FIG. 3 is a high level flowchart of a method according to some embodiments of the present invention. Method 300 may include measuring mobility parameters of a human body 310; measuring physiological parameters of said human body 320; measuring environmental parameters indicative of an environment of said human body 330; and applying a decision function configured to determine a predefined life endangering condition of said human body, based on said measured mobility, physiological, and environmental parameters, and statistical relationship therebetween 340.

Figure 4:
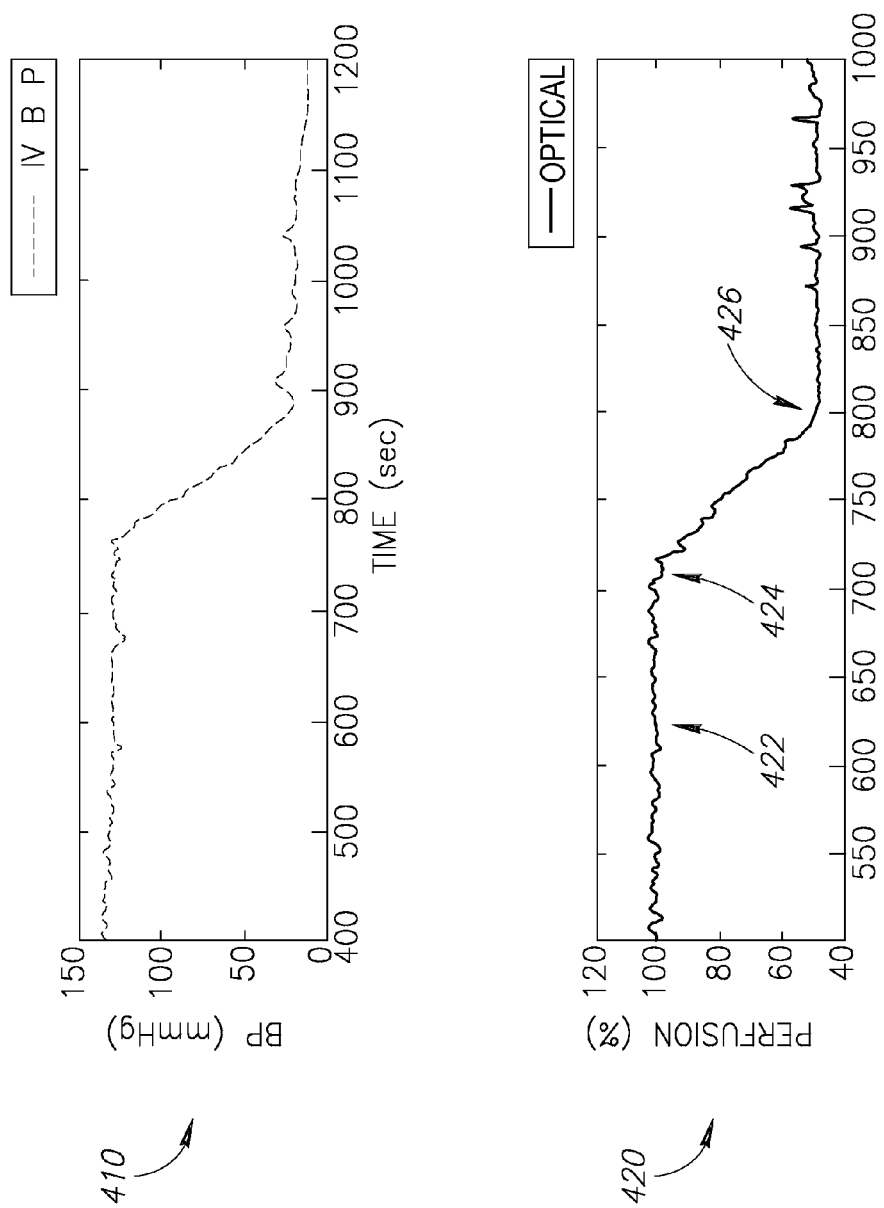
FIG. 4 shows graphs illustrating an aspect according to some embodiments of the present invention.

FIG. 4 shows graphs illustrating an aspect according to some embodiments of the present invention. The upper graph 410 shows actual measurements of blood flow taken from a sensor located within a bleeding animal. The lower graph 420 illustrates simultaneous optical measurements of the same animal. Point 422 is normal perfusion, 424 a decrease starts (endangering condition) and 426 indicates death. It can be clearly seen that both signals behave similarly, which serves as an enabler for using optical sensing as a substitute for direct blood flow measurements.

As will be appreciated by one skilled in the art, some aspects of the present invention may be embodied as a system, method or an apparatus. Accordingly, some aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system."

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system comprising:
   (a) at least one mobility sensor configured for measuring at least one mobility parameter of a user;
   (b) at least one physiological sensor configured for sensing a Brownian criterion and a chaotic flow criterion and quantify chaotic flow behavior of blood flowing at different arterioles of said user; and
   (c) a processor configured to detect a change in said at least one mobility parameter and a correlatable change in said chaotic flow behavior of said blood and apply a decision function to determine if said user deviated from a specified normal condition,
   wherein the system is configured to transmit an alert signal of a potentially life endangering situation when said user deviates from said specified normal condition.

2. The system according to claim 1, wherein the at least one physiological sensor is configured to extract a dynamic light scattering (DLS) signal.

3. The system according to claim 2, wherein the Brownian criterion is extracted by the measuring a decay time of an autocorrelation function of the DLS signal.

4. The system according to claim 2, wherein the chaotic flow criterion is extracted by the measuring a correlation between a flow of red blood cells particles at different arterioles, based on the DLS signal.

5. The system according to claim 1, wherein said processor is further configured for detecting a change in said at least one environmental parameter and correlating said change in said at least one environmental parameter with said change in said at least one mobility parameter and/or said change in said chaotic flow behavior of said blood.

6. The system according to claim 5, wherein said at least one mobility sensor and said at least one physiological sensors are configured to be worn on a body of said user.

7. The system of claim 1, further comprising at least one environmental sensor configured for measuring at least one environmental parameter in an environment surrounding said user.

8. A method comprising:
   measuring at least one mobility parameter of a user;
   sensing a Brownian criterion and a chaotic flow criterion and quantify chaotic flow behavior of blood flowing at different arterioles of said user; and
   detecting a change in said at least one mobility parameter and a correlatable change in said chaotic flow behavior of said blood and applying a decision function to determine if said user deviated from a specified normal condition; and
   transmitting an alert signal of a potentially life endangering situation when said user deviates from said specified normal condition.

9. The method according to claim 8 wherein said Brownian criterion and said chaotic flow criterion are derived via Dynamic Light Scattering (DLS) defined by an DLS signal.

10. The method according to claim 9, wherein the Brownian criterion is extracted by measuring a decay time of an autocorrelation function of the DLS signal.

11. The method according to claim 9, wherein the chaotic flow criterion is extracted by the measuring a correlation between a flow of red blood cells particles at different arterioles, based on the DLS signal.

12. The method of claim 8, further comprising measuring at least one environmental parameter in an environment surrounding said user.

13. The method of claim 12, further detecting a change in said at least one environmental parameter and correlating said change in said at least one environmental parameter with said change in said at least one mobility parameter and/or said change in said chaotic flow behavior of said blood.

* * * * *